United States Patent [19]

Houlihan et al.

[11] 3,941,888

[45] Mar. 2, 1976

[54] SUBSTITUTED OR UNSUBSTITUTED P-ALKANOYL TOLUENES AS HYPOLIPIDEMICS

[75] Inventors: William J. Houlihan, Mountain Lakes; Jeffrey Nadelson, Lake Parsippany, both of N.J.

[73] Assignee: Sandoz, Inc., E. Hanover, N.J.

[22] Filed: Feb. 3, 1975

[21] Appl. No.: 546,755

Related U.S. Application Data

[63] Continuation-in-part of Ser. No. 495,862, Aug. 8, 1974, abandoned.

[52] U.S. Cl. .............................................. 424/331
[51] Int. Cl.² ........................................ A61K 31/12
[58] Field of Search ..................................... 424/331

[56] References Cited

OTHER PUBLICATIONS

Journal American Chemical Society, 93:16, 8/11/71.

Primary Examiner—Frederick E. Waddell
Attorney, Agent, or Firm—Gerald D. Sharkin; Robert S. Honor

[57] ABSTRACT

Certain substituted or unsubstituted p-alkanoyl toluenes, e.g., p-alkanoyl toluene, are useful as hypolipidemic agents.

7 Claims, No Drawings

SUBSTITUTED OR UNSUBSTITUTED P-ALKANOYL TOLUENES AS HYPOLIPIDEMICS

This application is a continuation-in-part of copending application Ser. No. 495,862, filed Aug. 8, 1974, now abandoned.

This invention relates to the pharmaceutical activity of p-alkanoyl toluenes. More particularly, this invention concerns the use of substituted or unsubstituted p-alkanoyl toluenes in the treatment of lipidemia. The invention also relates to pharmaceutical compositions containing these compounds as an active ingredient thereof.

The active agents with which this invention is concerned may be represented by the following structural formula:

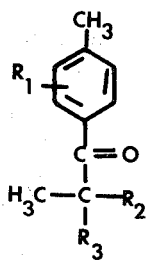

(I)

where $R_1$ represents hydrogen, halo having an atomic weight of about 19 to 36, and straight chain lower alkoxy, i.e., straight chain alkoxy having 1 to 4 carbon atoms, e.g., methoxy, ethoxy, isopropoxy or the like, and $R_2$ and $R_3$ each independently represent alkyl having 1 or 2 carbon atoms, i.e., methyl or ethyl.

The compounds of formula (I) above are known and may be prepared according to methods disclosed in the literature from known materials. The present invention contemplates only the novel use of such compounds as hypolipidemic agents.

The compounds of formula (I) are useful because they possess pharmacological activity in animals as hypolipidemic agents, particularly as hypolipoproteinemic agents as indicated by the fall in cholesterol and triglyceride levels in male albino Wistar rats weighing 110–130 g. initially. The rats are maintained on drug-free laboratory chow diet for seven days and then divided into groups of 8 to 10 animals. Each group with the exception of the control is then given orally 30 to 200 milligrams per kilogram of body weight per diem of the compound for six days. At the end of this period, the animals are anesthetized with sodium hexobarbital and bled from the carotid arteries. Serum or plasma samples are collected, and 1.0 ml. samples of the serum are added to 9.0 ml. redistilled isopropanol. Two autoanalyzer cupsful of a mixture of zeolite-copper hydroxide and Lloydds reagent (Kessler, G., and Lederer, H., 1965, Technicon Symposium, Mediad Inc., New York [345, 347]) are added, and the mixture is shaken for one hour. Cholesterol and triglyceride levels are determined simultaneously on the same sample by Technicon N-24 A (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels are then computed and the hypocholesterolemic acitivity is expressed as the fall in cholesterol levels as a percentage of the control level. The change in serum triglyceride levels induced by the drug is computed as a percentage of the control triglyceride levels.

For such usage, the compounds of formula (I) may be administered orally or parenterally as such or admixed with conventional pharmaceutical carriers. They may be administered orally in such forms as tablets, dispersible powders, soft gelatin capsules, capsules, emulsions, preferably soft gelatin capsules, and parenterally as emulsions, e.g., a sterile injectable emulsion. The compositions for oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., starch and alginic acid, binding agents, e.g., starch, gelatin and acacia, lubricating agents, e.g., magnesium stearate, stearic acid and talc, and absorbing agents such as colloidal silicon dioxide. The tablets may be coated or uncoated by known techniques to delay disintegration and absorption in the gastro-intestinal tract and thereby provide a sustained action over a longer period. Similarly, suspensions and emulsions may contain the active ingredient in admixture with any of the conventional excipients utilized by the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl-p-hydroxybenzoate. Capsules may contain the active ingredient admixed with an inert solid diluent, e.g., calcium carbonate, calcium phosphate and kaolin. Soft gelatin capsules may contain the active ingredient in admixture with conventional pharmaceutical excipients, e.g., inert carriers such as vegetable oils (soybean oil, corn oil and the like), polyethyleneglycol derivatives or mineral oils. The injectable compositions are formulated as known in the art. These pharmaceutical preparations may contain up to about 90% of the active ingredient in combination with the carrier or adjuvant.

The hypolipidemic effective dosage of compounds (I) employed in the alleviation of lipidemia may vary depending on the particular compound employed and the severity of the condition being treated. However, in general, satisfactory results are obtained when the compounds of formula (I) are administered at a daily dosage of from about 1.0 milligrams to about 250 milligrams per kilogram of animal body weight given in divided doses 2 to 4 times a day, or in sustained release form. For most large mammals, the total daily dosage is from about 75 milligrams to about 2500 milligrams. Dosage forms suitable for internal use comprise from about 18 to about 1250 milligrams of the active compound in intimate admixture with a solid or liquid pharmaceutically acceptable carrier or diluent.

Compounds of formula (I) which can be used as the active ingredient include the following:

a. 2-chloro-4-pivaloyl toluene,
b. 2-methoxy-4-pivaloyl toluene, or
c. p-pivaloyl toluene, the latter being especially preferred.

A representative formulation suitable for oral administration is a tablet, capsule or soft gelatin capsule prepared by standard tabletting or encapsulating techniques which contains the following and may be administered 2 to 4 times a day in the treatment of lipidemia.

EXAMPLE 1

| Ingredient | Weight (mg.) |
|---|---|
| | Capsule |
| p-pivaloyl toluene | 100 |
| tragacanth | — |
| lactose | 300 |
| corn starch | — |
| talcum | — |
| magnesium stearate | — |
| Total | 400 mg. |

| Ingredient | Weight (mg.) | | |
|---|---|---|---|
| | tablet | capsule | soft gelatin capsule |
| p-pivaloyl toluene | 100 | 100 | 100 |
| polyvinylpyrrolidone | 15 | — | — |
| lactose | 282.5 | 346 | — |
| corn starch | 25 | — | — |
| talcum | 15 | — | — |
| colloidal silicon dioxide | 50 | 50 | — |
| magnesium stearate | 2.5 | — | — |
| stearic acid | — | 4 | — |
| soybean oil | — | — | 300 |
| | 500 mg. | 500 mg. | 400 mg. |

The following pharmaceutical compositions are formulated with the indicated amount of active agent using conventional techniques. The injectable emulsion, the oral liquid suspension, and the oral liquid emulsion represent formulations useful as unit doses and may be administered in the treatment of lipidemia. The injectable emulsion is suitable for administration once or twice a day whereas the oral liquid suspension and the oral liquid emulsion is suitably administered 2 to 4 times per day for this purpose.

EXAMPLE 3

| Ingredient | Weight (mg.) |
|---|---|
| | Oral liquid suspension |
| p-pivaloyl toluene | 100 |
| sodium carobxy methylcellulose, U.S.P. | 12.5 |
| magnesium aluminum silicate | 47.5 |
| flavor | q.s. |
| color | q.s. |
| methyl paraben, U.S.P. | 4.5 |
| propyl paraben, U.S.P. | 1.0 |
| polysorbate 90 (e.g., Tween 80), U.S.P. | 5 |
| sorbitol solution, 70%, U.S.P. | 2,500 |
| buffer agent to adjust pH for desired stability | q.s. |
| water | q.s. to 5 ml. |

EXAMPLE 4

| Ingredient | Weight (mg.) | |
|---|---|---|
| | Sterile injectable emulsion | Oral liquid emulsion |
| p-pivaloyl toluene | 200 | 100 |
| sodium, carboxy methyl- | | |
| cellulose, U.S.P. | — | 12.5 |
| polyvinylpyrrolidone | 5 | — |
| benzoyl alcohol | 0.01 | — |
| sodium chloride | to be adjusted to an isotonic concentration | — |
| flavor | — | q.s. |
| color | — | q.s. |
| methyl paraben, U.S.P. | — | 4.5 |
| propyl paraben, U.S.P. | — | 1.0 |
| polysorbate 80 (e.g., Tween 80), U.S.P. | 1 | 5 |
| sorbitol solution, 70% U.S.P. | — | 2,500 |
| buffer agent to adjust pH for desired stability | q.s. | q.s. |
| water | for injection q.s. to 1 ml. | q.s. to 5 ml. |

The preferred pharmaceutical compositions from the standpoint of preparation and ease of administration are soft gelatin capsules containing from about 100 to 200 milligrams of the active ingredient.

What is claimed is:

1. A method for treating lipidemia which comprises administering to a mammal in need of said treatment a hypolipidemic effective amount of a compound of the formula:

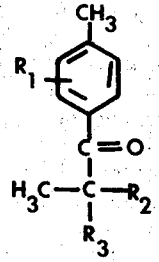

where
$R_1$ represents hydrogen, halo having an atomic weight of about 19 to 36, or straight chain lower alkoxy having 1 to 4 carbon atoms, and
$R_2$ and $R_3$ each independently represent alkyl having 1 to 2 carbon atoms.

2. The method of claim 1 in which the compound is

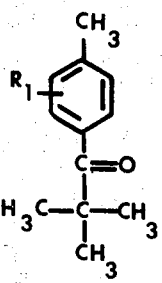

where $R_1$ is as defined in claim 1.

3. The method of claim 1 in which the compound is p-pivaloyl toluene.

4. The method of claim 1 wherein the compound is administered orally at a daily dosage of from about 75 milligrams to about 2500 milligrams.

5. The method of claim 1 wherein the compound is orally administered in a unit dosage form comprising said compound to the extent of from about 18 milligrams to about 1250 milligrams per unit dosage.

6. A pharmaceutical composition in dosage form suitable for internal use as a hypolipidemic agent comprising as an active ingredient thereof a compound of the formula:

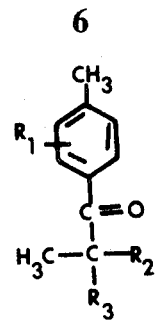

where $R_1$, $R_2$, and $R_3$ are as defined in claim 1, and a pharmaceutically acceptable carrier therefor, said compound being present in an amount from 18 milligrams to 1250 milligrams.

7. The composition of claim 6 in which the active ingredient is p-pivaloyl toluene.

* * * * *